US00RE43328E

(19) United States
(12) Reissued Patent
Foley et al.

(10) Patent Number: US RE43,328 E
(45) Date of Reissued Patent: Apr. 24, 2012

(54) IMAGE GUIDED AWL/TAP/SCREWDRIVER

(75) Inventors: Kevin T. Foley, Memphis, TN (US); Anthony J. Melkent, Lafayette, CO (US); Catalina J. Carroll, Memphis, TN (US)

(73) Assignee: Medtronic Navigation, Inc, Louisville, CO (US)

(21) Appl. No.: 10/062,265

(22) Filed: Jan. 31, 2002

Related U.S. Patent Documents

Reissue of:
(64) Patent No.: 6,021,343
Issued: Feb. 1, 2000
Appl. No.: 08/971,126
Filed: Nov. 20, 1997

(51) Int. Cl.
*A61B 5/05* (2006.01)

(52) U.S. Cl. ..... 600/429; 600/417; 600/407; 600/473; 600/476; 606/130; 606/79; 606/80; 606/96; 606/60; 606/61; 606/62; 606/104

(58) Field of Classification Search ..... 600/429, 600/417, 407, 473, 476; 606/130, 79, 80, 606/96, 60–62, 104
See application file for complete search history.

(56) References Cited

U.S. PATENT DOCUMENTS

| | | | |
|---|---|---|---|
| 1,576,781 | A | 3/1926 | Phillips |
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Sehnder |
| 3,016,899 | A | 1/1962 | Stenvall |
| 3,017,887 | A | 1/1962 | Heyer |
| 3,061,936 | A | 11/1962 | Dobbeleer |
| 3,073,310 | A | 1/1963 | Mocarski |
| 3,109,588 | A | 11/1963 | Polhemus et al. |
| 3,294,083 | A | 12/1966 | Alderson |
| 3,367,326 | A | 2/1968 | Frazier |
| 3,439,256 | A | 4/1969 | Kähne et al. |
| 3,577,160 | A | 5/1971 | White |
| 3,614,950 | A | 10/1971 | Rabey |
| 3,644,825 | A | 2/1972 | Davis, Jr. et al. |

(Continued)

FOREIGN PATENT DOCUMENTS

| | | |
|---|---|---|
| CA | 964149 | 3/1975 |

(Continued)

OTHER PUBLICATIONS

Barrick, "Distal Locking Screw Insertion Using a Cannulated Drill Bit: Technical Note," Journal of Orthopaedic Trauma, vol. 7, No. 3, 1993, pp. 248-251.

(Continued)

*Primary Examiner* — Tse Chen
*Assistant Examiner* — Mark Remaly
(74) *Attorney, Agent, or Firm* — Harness, Dickey

(57) ABSTRACT

A trackable medical instrument for use in a computer assisted image guided medical and surgical navigation systems that generate images during medical and surgical procedures, includes a guide member having an emitter array for being tracked by the system and a drive shaft contained within the guide member having a proximal and a distal end, the drive shaft being rotatable within the guide member while being fixable axially inside the guide member, the proximal end of the drive shaft having a first connector for interchangeably receiving at least one drive source, and the distal end having a second connector for interchangeably receiving at least one instrument tip.

88 Claims, 5 Drawing Sheets

U.S. PATENT DOCUMENTS

| | | | |
|---|---|---|---|
| 3,674,014 | A | 7/1972 | Tillander |
| 3,702,935 | A | 11/1972 | Carey et al. |
| 3,704,707 | A | 12/1972 | Halloran |
| 3,821,469 | A | 6/1974 | Whetstone et al. |
| 3,868,565 | A | 2/1975 | Kuipers |
| 3,941,127 | A | 3/1976 | Froning |
| 3,963,028 | A | 6/1976 | Cooley et al. |
| 3,983,474 | A | 9/1976 | Kuipers |
| 4,017,858 | A | 4/1977 | Kuipers |
| 4,037,592 | A | 7/1977 | Kronner |
| 4,052,620 | A | 10/1977 | Brunnett |
| 4,054,881 | A | 10/1977 | Raab |
| 4,117,337 | A | 9/1978 | Staats |
| 4,173,228 | A | 11/1979 | Van Steenwyk et al. |
| 4,182,312 | A | 1/1980 | Mushabac |
| 4,202,349 | A | 5/1980 | Jones |
| 4,228,799 | A | 10/1980 | Anichkov et al. |
| 4,256,112 | A | 3/1981 | Kopf et al. |
| 4,262,306 | A | 4/1981 | Renner |
| 4,287,809 | A | 9/1981 | Egli et al. |
| 4,298,874 | A | 11/1981 | Kuipers |
| 4,314,251 | A | 2/1982 | Raab |
| 4,317,078 | A | 2/1982 | Weed et al. |
| 4,319,136 | A | 3/1982 | Jinkins |
| 4,328,548 | A | 5/1982 | Crow et al. |
| 4,328,813 | A | 5/1982 | Ray |
| 4,339,953 | A | 7/1982 | Iwasaki |
| 4,341,220 | A | 7/1982 | Perry |
| 4,346,384 | A | 8/1982 | Raab |
| 4,358,856 | A | 11/1982 | Stivender et al. |
| 4,368,536 | A | 1/1983 | Pfeiler |
| 4,396,885 | A | 8/1983 | Constant |
| 4,396,945 | A | 8/1983 | DiMatteo et al. |
| 4,403,321 | A | 9/1983 | DiMarco |
| 4,418,422 | A | 11/1983 | Richter et al. |
| 4,419,012 | A | 12/1983 | Stephenson et al. |
| 4,422,041 | A | 12/1983 | Lienau |
| 4,431,005 | A | 2/1984 | McCormick |
| 4,485,815 | A | 12/1984 | Amplatz |
| 4,506,676 | A | 3/1985 | Duska |
| 4,543,959 | A | 10/1985 | Sepponen |
| 4,548,208 | A | 10/1985 | Niemi |
| 4,571,834 | A | 2/1986 | Fraser et al. |
| 4,572,198 | A | 2/1986 | Codrington |
| 4,583,538 | A | 4/1986 | Onik et al. |
| 4,584,577 | A | 4/1986 | Temple |
| 4,608,977 | A | 9/1986 | Brown |
| 4,613,866 | A | 9/1986 | Blood |
| 4,617,925 | A | 10/1986 | Laitinen |
| 4,618,978 | A | 10/1986 | Cosman |
| 4,621,628 | A | 11/1986 | Bludermann |
| 4,625,718 | A | 12/1986 | Olerud et al. |
| 4,638,798 | A | 1/1987 | Shelden et al. |
| 4,642,786 | A | 2/1987 | Hansen |
| 4,645,343 | A | 2/1987 | Stockdale et al. |
| 4,649,504 | A | 3/1987 | Krouglicof et al. |
| 4,651,732 | A | 3/1987 | Frederick |
| 4,653,509 | A | 3/1987 | Oloff et al. |
| 4,659,971 | A | 4/1987 | Suzuki et al. |
| 4,660,970 | A | 4/1987 | Ferrano |
| 4,672,306 | A | 6/1987 | Thong |
| 4,673,352 | A | 6/1987 | Hansen |
| 4,688,037 | A | 8/1987 | Krieg |
| 4,701,049 | A | 10/1987 | Beckmann et al. |
| 4,705,395 | A | 11/1987 | Hageniers |
| 4,705,401 | A | 11/1987 | Addleman et al. |
| 4,706,665 | A | 11/1987 | Gouda |
| 4,709,156 | A | 11/1987 | Murphy et al. |
| 4,710,708 | A | 12/1987 | Rorden et al. |
| 4,719,419 | A | 1/1988 | Dawley |
| 4,722,056 | A | 1/1988 | Roberts et al. |
| 4,722,336 | A | 2/1988 | Kim et al. |
| 4,723,544 | A | 2/1988 | Moore et al. |
| 4,727,565 | A | 2/1988 | Ericson |
| RE32,619 | E | 3/1988 | Damadian |
| 4,733,969 | A | 3/1988 | Case et al. |
| 4,737,032 | A | 4/1988 | Addleman et al. |
| 4,737,794 | A | 4/1988 | Jones |
| 4,737,921 | A | 4/1988 | Goldwasser et al. |
| 4,742,356 | A | 5/1988 | Kuipers |
| 4,742,815 | A | 5/1988 | Ninan et al. |
| 4,743,770 | A | 5/1988 | Lee |
| 4,743,771 | A | 5/1988 | Sacks et al. |
| 4,745,290 | A | 5/1988 | Frankel et al. |
| 4,750,487 | A | 6/1988 | Zanetti |
| 4,753,528 | A | 6/1988 | Hines et al. |
| 4,761,072 | A | 8/1988 | Pryor |
| 4,764,016 | A | 8/1988 | Johansson |
| 4,771,787 | A | 9/1988 | Wurster et al. |
| 4,779,212 | A | 10/1988 | Levy |
| 4,782,239 | A | 11/1988 | Hirose et al. |
| 4,788,481 | A | 11/1988 | Niwa |
| 4,791,934 | A | 12/1988 | Brunnett |
| 4,793,355 | A | 12/1988 | Crum et al. |
| 4,794,262 | A | 12/1988 | Sato et al. |
| 4,797,907 | A | 1/1989 | Anderton |
| 4,803,976 | A | 2/1989 | Frigg et al. |
| 4,804,261 | A | 2/1989 | Kirschen |
| 4,805,615 | A | 2/1989 | Carol |
| 4,809,694 | A | 3/1989 | Ferrara |
| 4,821,200 | A | 4/1989 | Öberg |
| 4,821,206 | A | 4/1989 | Arora |
| 4,821,731 | A | 4/1989 | Martinelli et al. |
| 4,822,163 | A | 4/1989 | Schmidt |
| 4,825,091 | A | 4/1989 | Breyer et al. |
| 4,829,373 | A | 5/1989 | Leberl et al. |
| 4,836,778 | A | 6/1989 | Baumrind et al. |
| 4,838,265 | A | 6/1989 | Cosman et al. |
| 4,841,967 | A | 6/1989 | Chang et al. |
| 4,845,771 | A | 7/1989 | Wislocki et al. |
| 4,849,692 | A | 7/1989 | Blood |
| 4,860,331 | A | 8/1989 | Williams et al. |
| 4,862,893 | A | 9/1989 | Martinelli |
| 4,869,247 | A | 9/1989 | Howard, III et al. |
| 4,875,165 | A | 10/1989 | Fencil et al. |
| 4,875,478 | A | 10/1989 | Chen |
| 4,884,566 | A | 12/1989 | Mountz et al. |
| 4,889,526 | A | 12/1989 | Rauscher et al. |
| 4,896,673 | A | 1/1990 | Rose et al. |
| 4,905,698 | A | 3/1990 | Strohl, Jr. et al. |
| 4,923,459 | A | 5/1990 | Nambu |
| 4,931,056 | A | 6/1990 | Ghajar et al. |
| 4,945,305 | A | 7/1990 | Blood |
| 4,945,914 | A | 8/1990 | Allen |
| 4,951,653 | A | 8/1990 | Fry et al. |
| 4,955,891 | A | 9/1990 | Carol |
| 4,961,422 | A | 10/1990 | Marchosky et al. |
| 4,977,655 | A | 12/1990 | Martinelli |
| 4,989,608 | A | 2/1991 | Ratner |
| 4,991,579 | A | 2/1991 | Allen |
| 5,002,058 | A | 3/1991 | Martinelli |
| 5,005,592 | A | 4/1991 | Cartmell |
| 5,013,317 | A | 5/1991 | Cole et al. |
| 5,016,639 | A | 5/1991 | Allen |
| 5,017,139 | A | 5/1991 | Mushabac |
| 5,027,818 | A | 7/1991 | Bova et al. |
| 5,030,196 | A | 7/1991 | Inoue |
| 5,030,222 | A | 7/1991 | Calandruccio et al. |
| 5,031,203 | A | 7/1991 | Trecha |
| 5,042,486 | A | 8/1991 | Pfeiler et al. |
| 5,047,036 | A | 9/1991 | Koutrouvelis |
| 5,050,608 | A | 9/1991 | Watanabe et al. |
| 5,054,492 | A | 10/1991 | Scribner et al. |
| 5,057,095 | A | 10/1991 | Fabian |
| 5,059,789 | A | 10/1991 | Salcudean |
| 5,078,140 | A | 1/1992 | Kwoh |
| 5,079,699 | A | 1/1992 | Tuy et al. |
| 5,086,401 | A | 2/1992 | Glassman et al. |
| 5,094,241 | A | 3/1992 | Allen |
| 5,097,839 | A | 3/1992 | Allen |
| 5,098,426 | A | 3/1992 | Sklar et al. |
| 5,099,845 | A | 3/1992 | Besz et al. |
| 5,099,846 | A | 3/1992 | Hardy |
| 5,105,829 | A | 4/1992 | Fabian et al. |
| 5,107,839 | A | 4/1992 | Houdek et al. |
| 5,107,843 | A | 4/1992 | Aarnio et al. |
| 5,107,862 | A | 4/1992 | Fabian et al. |

| | | | |
|---|---|---|---|
| 5,109,194 | A | 4/1992 | Cantaloube |
| 5,119,817 | A | 6/1992 | Allen |
| 5,142,930 | A | 9/1992 | Allen et al. |
| 5,143,076 | A | 9/1992 | Hardy et al. |
| 5,152,288 | A | 10/1992 | Hoenig et al. |
| 5,160,337 | A | 11/1992 | Cosman |
| 5,161,536 | A | 11/1992 | Vikomerson et al. |
| 5,178,164 | A | 1/1993 | Allen |
| 5,178,621 | A | 1/1993 | Cook et al. |
| 5,186,174 | A | 2/1993 | Schlondorff et al. |
| 5,187,475 | A | 2/1993 | Wagener et al. |
| 5,188,126 | A | 2/1993 | Fabian et al. |
| 5,190,059 | A | 3/1993 | Fabian et al. |
| 5,193,106 | A | 3/1993 | DeSena |
| 5,197,476 | A | 3/1993 | Nowacki et al. |
| 5,197,965 | A | 3/1993 | Cherry et al. |
| 5,198,768 | A | 3/1993 | Keren |
| 5,198,877 | A | 3/1993 | Schulz |
| 5,207,681 | A | 5/1993 | Ghadjar et al. |
| 5,207,688 | A | 5/1993 | Carol |
| 5,211,164 | A | 5/1993 | Allen |
| 5,211,165 | A | 5/1993 | Dumoulin et al. |
| 5,211,176 | A | 5/1993 | Ishiguro et al. |
| 5,212,720 | A | 5/1993 | Landi et al. |
| 5,214,615 | A | 5/1993 | Bauer |
| 5,219,351 | A | 6/1993 | Teubner et al. |
| 5,222,499 | A | 6/1993 | Allen et al. |
| 5,224,049 | A | 6/1993 | Mushabac |
| 5,228,442 | A | 7/1993 | Imran |
| 5,230,338 | A | 7/1993 | Allen et al. |
| 5,230,623 | A | 7/1993 | Guthrie et al. |
| 5,233,990 | A | 8/1993 | Barnea |
| 5,237,996 | A | 8/1993 | Waldman et al. |
| 5,249,581 | A | 10/1993 | Horbal et al. |
| 5,251,127 | A | 10/1993 | Raab |
| 5,251,635 | A | 10/1993 | Dumoulin et al. |
| 5,253,647 | A | 10/1993 | Takahashi et al. |
| 5,255,680 | A | 10/1993 | Darrow et al. |
| 5,257,636 | A | 11/1993 | White |
| 5,257,998 | A | 11/1993 | Ota et al. |
| 5,261,404 | A | 11/1993 | Mick et al. |
| 5,265,610 | A | 11/1993 | Darrow et al. |
| 5,265,611 | A | 11/1993 | Hoenig et al. |
| 5,269,759 | A | 12/1993 | Hernandez et al. |
| 5,271,400 | A | 12/1993 | Dumoulin et al. |
| 5,273,025 | A | 12/1993 | Sakiyama et al. |
| 5,274,551 | A | 12/1993 | Corby, Jr. |
| 5,279,309 | A | 1/1994 | Taylor et al. |
| 5,285,787 | A | 2/1994 | Machida |
| 5,291,199 | A | 3/1994 | Overman et al. |
| 5,291,889 | A | 3/1994 | Kenet et al. |
| 5,295,483 | A | 3/1994 | Nowacki et al. |
| 5,297,549 | A | 3/1994 | Beatty et al. |
| 5,299,253 | A | 3/1994 | Wessels |
| 5,299,254 | A | 3/1994 | Dancer et al. |
| 5,299,288 | A | 3/1994 | Glassman et al. |
| 5,300,080 | A | 4/1994 | Clayman et al. |
| 5,305,091 | A | 4/1994 | Gelbart et al. |
| 5,305,203 | A | 4/1994 | Raab |
| 5,306,271 | A | 4/1994 | Zinreich et al. |
| 5,307,072 | A | 4/1994 | Jones, Jr. |
| 5,309,913 | A | 5/1994 | Kormos et al. |
| 5,315,630 | A | 5/1994 | Sturm et al. |
| 5,316,024 | A | 5/1994 | Hirschi et al. |
| 5,318,025 | A | 6/1994 | Dumoulin et al. |
| 5,320,111 | A | 6/1994 | Livingston |
| 5,325,728 | A | 7/1994 | Zimmerman et al. |
| 5,325,873 | A | 7/1994 | Hirschi et al. |
| 5,329,944 | A | 7/1994 | Fabian et al. |
| 5,330,485 | A | 7/1994 | Clayman et al. |
| 5,333,168 | A | 7/1994 | Fernandes et al. |
| 5,353,795 | A | 10/1994 | Souza et al. |
| 5,353,800 | A | 10/1994 | Pohndorf et al. |
| 5,353,807 | A | 10/1994 | DeMarco |
| 5,359,417 | A | 10/1994 | Müller et al. |
| 5,368,030 | A | 11/1994 | Zinreich et al. |
| 5,371,778 | A | 12/1994 | Yanof et al. |
| 5,375,596 | A | 12/1994 | Twiss et al. |
| 5,377,678 | A | 1/1995 | Dumoulin et al. |
| 5,383,454 | A | 1/1995 | Bucholz |
| 5,385,146 | A | 1/1995 | Goldreyer |
| 5,385,148 | A | 1/1995 | Lesh et al. |
| 5,386,828 | A | 2/1995 | Owens et al. |
| 5,389,101 | A | 2/1995 | Heilbrun et al. |
| 5,391,199 | A | 2/1995 | Ben-Haim |
| 5,394,457 | A | 2/1995 | Leibinger et al. |
| 5,394,875 | A | 3/1995 | Lewis et al. |
| 5,397,329 | A | 3/1995 | Allen |
| 5,398,684 | A | 3/1995 | Hardy |
| 5,399,146 | A | 3/1995 | Nowacki et al. |
| 5,400,384 | A | 3/1995 | Fernandes et al. |
| 5,402,801 | A | 4/1995 | Taylor |
| 5,408,409 | A | 4/1995 | Glassman et al. |
| 5,413,573 | A | 5/1995 | Koivukangas |
| 5,417,210 | A | 5/1995 | Funda et al. |
| 5,419,325 | A | 5/1995 | Dumoulin et al. |
| 5,423,334 | A | 6/1995 | Jordan |
| 5,425,367 | A | 6/1995 | Shapiro et al. |
| 5,425,382 | A | 6/1995 | Golden et al. |
| 5,426,683 | A | 6/1995 | O'Farrell, Jr. et al. |
| 5,426,687 | A | 6/1995 | Goodall et al. |
| 5,427,097 | A | 6/1995 | Depp |
| 5,429,132 | A | 7/1995 | Guy et al. |
| 5,433,198 | A | 7/1995 | Desai |
| RE35,025 | E | 8/1995 | Anderton |
| 5,437,212 | A | 8/1995 | Thompson |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,444,756 | A | 8/1995 | Pai et al. |
| 5,445,144 | A | 8/1995 | Wodicka et al. |
| 5,445,150 | A | 8/1995 | Dumoulin et al. |
| 5,445,166 | A | 8/1995 | Taylor |
| 5,446,548 | A | 8/1995 | Gerig et al. |
| 5,447,154 | A | 9/1995 | Cinquin et al. |
| 5,448,610 | A | 9/1995 | Yamamoto et al. |
| 5,453,686 | A | 9/1995 | Anderson |
| 5,456,718 | A | 10/1995 | Szymaitis |
| 5,457,641 | A | 10/1995 | Zimmer et al. |
| 5,464,446 | A | 11/1995 | Dreessen et al. |
| 5,469,847 | A | 11/1995 | Zinreich et al. |
| 5,474,558 | A | 12/1995 | Neubardt |
| 5,478,341 | A | 12/1995 | Cook et al. |
| 5,478,343 | A | 12/1995 | Ritter |
| 5,480,422 | A | 1/1996 | Ben-Haim |
| 5,480,439 | A | 1/1996 | Bisek et al. |
| 5,483,961 | A | 1/1996 | Kelly et al. |
| 5,485,849 | A | 1/1996 | Panescu et al. |
| 5,487,391 | A | 1/1996 | Panescu |
| 5,487,729 | A | 1/1996 | Avellanet et al. |
| 5,487,757 | A | 1/1996 | Truckai et al. |
| 5,490,196 | A | 2/1996 | Rudich et al. |
| 5,494,034 | A | 2/1996 | Schlondorff et al. |
| 5,503,416 | A | 4/1996 | Aoki et al. |
| 5,513,637 | A | 5/1996 | Twiss et al. |
| 5,514,146 | A | 5/1996 | Lam et al. |
| 5,515,160 | A | 5/1996 | Schulz et al. |
| 5,517,990 | A | 5/1996 | Kalfas et al. |
| 5,531,227 | A | 7/1996 | Schneider |
| 5,531,520 | A | 7/1996 | Grimson et al. |
| 5,542,938 | A | 8/1996 | Avellanet et al. |
| 5,543,951 | A | 8/1996 | Moehrmann |
| 5,546,940 | A | 8/1996 | Panescu et al. |
| 5,546,949 | A | 8/1996 | Frazin et al. |
| 5,546,951 | A | 8/1996 | Ben-Haim |
| 5,551,429 | A | 9/1996 | Fitzpatrick et al. |
| 5,558,091 | A | 9/1996 | Acker et al. |
| 5,564,437 | A | 10/1996 | Bainville et al. |
| 5,566,681 | A | 10/1996 | Manwaring et al. |
| 5,568,384 | A | 10/1996 | Robb et al. |
| 5,568,809 | A | 10/1996 | Ben-haim |
| 5,572,999 | A | 11/1996 | Funda et al. |
| 5,573,533 | A | 11/1996 | Strul |
| 5,575,192 | A | 11/1996 | Eggert |
| 5,575,794 | A | 11/1996 | Walus et al. |
| 5,575,798 | A | 11/1996 | Koutrouvelis |
| 5,583,909 | A | 12/1996 | Hanover |
| 5,588,430 | A | 12/1996 | Bova et al. |

5,590,215 A 12/1996 Allen
5,591,207 A 1/1997 Coleman
5,592,939 A 1/1997 Martinelli
5,595,193 A 1/1997 Walus et al.
5,596,228 A 1/1997 Anderton et al.
5,600,330 A 2/1997 Blood
5,603,318 A 2/1997 Heilbrun et al.
5,611,025 A 3/1997 Lorensen et al.
5,617,462 A 4/1997 Spratt
5,617,857 A * 4/1997 Chader et al. ..... 600/424
5,619,261 A 4/1997 Anderton
5,622,169 A 4/1997 Golden et al.
5,622,170 A 4/1997 Schulz
5,627,873 A 5/1997 Hanover et al.
5,628,315 A 5/1997 Vilsmeier et al.
5,630,431 A 5/1997 Taylor
5,636,644 A 6/1997 Hart et al.
5,638,819 A 6/1997 Manwaring et al.
5,640,170 A 6/1997 Anderson
5,642,395 A 6/1997 Anderton et al.
5,643,268 A 7/1997 Vilsmeier et al.
5,645,065 A 7/1997 Shapiro et al.
5,645,545 A * 7/1997 Bryant ..... 606/62
5,646,524 A 7/1997 Gilboa
5,647,361 A 7/1997 Damadian
5,662,111 A 9/1997 Cosman
5,664,001 A 9/1997 Tachibana et al.
5,674,296 A 10/1997 Bryan et al.
5,676,673 A 10/1997 Ferre et al.
5,681,260 A 10/1997 Ueda et al.
5,682,886 A 11/1997 Delp et al.
5,682,890 A * 11/1997 Kormos et al. ..... 600/417
5,690,108 A 11/1997 Chakeres
D387,427 S 12/1997 Bucholz et al.
5,694,945 A 12/1997 Ben-Haim
5,695,500 A 12/1997 Taylor et al.
5,695,501 A 12/1997 Carol et al.
5,697,377 A 12/1997 Wittkampf
5,702,406 A 12/1997 Vilsmeier et al.
5,711,299 A 1/1998 Manwaring et al.
5,713,946 A 2/1998 Ben-Haim
5,715,822 A 2/1998 Watkins
5,715,836 A 2/1998 Kliegis et al.
5,718,241 A 2/1998 Ben-Haim et al.
5,727,552 A 3/1998 Ryan
5,727,553 A 3/1998 Saad
5,729,129 A 3/1998 Acker
5,730,129 A 3/1998 Darrow et al.
5,730,130 A 3/1998 Fitzpatrick et al.
5,732,703 A * 3/1998 Kalfas et al. ..... 600/407
5,735,278 A 4/1998 Hoult et al.
5,738,096 A 4/1998 Ben-Haim
5,740,802 A 4/1998 Nafis et al.
5,741,214 A 4/1998 Ouchi et al.
5,742,394 A 4/1998 Hansen
5,744,953 A 4/1998 Hansen
5,748,767 A 5/1998 Raab
5,749,362 A 5/1998 Funda et al.
5,749,835 A 5/1998 Glantz
5,752,513 A 5/1998 Acker et al.
5,755,725 A 5/1998 Druais
RE35,816 E 6/1998 Schulz
5,758,667 A 6/1998 Slettenmark
5,762,064 A 6/1998 Polyani
5,767,669 A 6/1998 Hansen et al.
5,767,960 A 6/1998 Orman
5,769,789 A 6/1998 Wang et al.
5,769,843 A 6/1998 Abela et al.
5,769,861 A 6/1998 Vilsmeier
5,772,594 A 6/1998 Barrick
5,775,322 A 7/1998 Silverstein et al.
5,776,064 A 7/1998 Kalfas et al.
5,782,765 A 7/1998 Jonkman
5,787,886 A 8/1998 Kelly et al.
5,792,055 A 8/1998 McKinnon
5,795,294 A 8/1998 Luber et al.
5,797,849 A 8/1998 Vesely et al.
5,799,055 A 8/1998 Peshkin et al.
5,799,099 A 8/1998 Wang et al.
5,800,352 A 9/1998 Ferre et al.
5,800,535 A 9/1998 Howard, III
5,802,719 A 9/1998 O'Farrell, Jr. et al.
5,803,089 A 9/1998 Ferre et al.
5,807,252 A 9/1998 Hassfeld et al.
5,810,008 A 9/1998 Dekel et al.
5,810,728 A 9/1998 Kuhn
5,810,735 A 9/1998 Halperin et al.
5,810,828 A 9/1998 Lightman et al.
5,820,553 A 10/1998 Hughes
5,823,192 A 10/1998 Kalend et al.
5,823,958 A 10/1998 Truppe
5,828,725 A 10/1998 Levinson
5,828,770 A 10/1998 Leis et al.
5,829,444 A 11/1998 Ferre et al.
5,831,260 A 11/1998 Hansen
5,833,608 A 11/1998 Acker
5,834,759 A 11/1998 Glossop
5,836,954 A 11/1998 Heilbrun et al.
5,840,024 A 11/1998 Taniguchi et al.
5,840,025 A 11/1998 Ben-Haim
5,843,076 A 12/1998 Webster, Jr. et al.
5,848,967 A 12/1998 Cosman
5,851,183 A 12/1998 Bucholz
5,865,846 A 2/1999 Bryan et al.
5,868,674 A 2/1999 Glowinski et al.
5,868,675 A 2/1999 Henrion et al.
5,871,445 A 2/1999 Bucholz
5,871,455 A 2/1999 Ueno
5,871,487 A 2/1999 Warner et al.
5,873,822 A 2/1999 Ferre et al.
5,882,304 A 3/1999 Ehnholm et al.
5,884,410 A 3/1999 Prinz
5,889,834 A 3/1999 Vilsmeier et al.
5,891,034 A 4/1999 Bucholz
5,891,157 A 4/1999 Day et al.
5,904,691 A 5/1999 Barnett et al.
5,907,395 A 5/1999 Schultz et al.
5,913,820 A 6/1999 Bladen et al.
5,920,395 A 7/1999 Schulz
5,921,992 A 7/1999 Costales et al.
5,923,727 A 7/1999 Navab
5,928,248 A 7/1999 Acker
5,938,603 A 8/1999 Ponzi
5,938,694 A 8/1999 Jaraczewski et al.
5,947,980 A 9/1999 Jensen et al.
5,947,981 A 9/1999 Cosman
5,950,629 A 9/1999 Taylor et al.
5,951,475 A 9/1999 Gueziec et al.
5,951,571 A 9/1999 Audette
5,954,647 A 9/1999 Bova et al.
5,957,844 A 9/1999 Dekel et al.
5,964,796 A 10/1999 Imran
5,967,980 A 10/1999 Ferre et al.
5,967,982 A 10/1999 Barnett
5,968,047 A 10/1999 Reed
5,971,997 A 10/1999 Guthrie et al.
5,976,156 A 11/1999 Taylor et al.
5,980,535 A 11/1999 Barnett et al.
5,983,126 A 11/1999 Wittkampf
5,987,349 A 11/1999 Schulz
5,987,960 A 11/1999 Messner et al.
5,999,837 A 12/1999 Messner et al.
5,999,840 A 12/1999 Grimson et al.
6,001,130 A 12/1999 Bryan et al.
6,006,126 A 12/1999 Cosman
6,006,127 A 12/1999 Van Der Brug et al.
6,013,087 A 1/2000 Adams et al.
6,014,580 A 1/2000 Blume et al.
6,016,439 A 1/2000 Acker
6,019,725 A 2/2000 Vesely et al.
6,024,408 A 2/2000 Greenberg et al.
6,050,724 A 4/2000 Schmitz et al.
6,059,718 A 5/2000 Taniguchi et al.
6,063,022 A 5/2000 Ben-Haim
6,071,288 A 6/2000 Carol et al.
6,073,043 A 6/2000 Schneider
6,076,008 A 6/2000 Bucholz
6,096,050 A 8/2000 Audette

| | | | |
|---|---|---|---|
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier |
| 6,233,476 | B1 | 5/2001 | Strommer et al. |
| 6,236,875 | B1 * | 5/2001 | Bucholz et al. ..... 600/407 |
| 6,246,231 | B1 | 6/2001 | Ashe |
| 6,259,942 | B1 | 7/2001 | Westermann et al. |
| 6,273,896 | B1 | 8/2001 | Franck et al. |
| 6,285,902 | B1 | 9/2001 | Kienzle, III et al. |
| 6,298,262 | B1 | 10/2001 | Franck et al. |
| 6,314,310 | B1 | 11/2001 | Ben-Haim et al. |
| 6,332,089 | B1 | 12/2001 | Acker et al. |
| 6,341,231 | B1 | 1/2002 | Ferre et al. |
| 6,351,659 | B1 | 2/2002 | Vilsmeier |
| 6,381,485 | B1 | 4/2002 | Hunter et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,516,046 | B1 | 2/2003 | Fröhlich et al. |
| 6,527,443 | B1 | 3/2003 | Vilsmeier et al. |
| 6,551,325 | B2 | 4/2003 | Neubauer et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |
| 6,694,162 | B2 | 2/2004 | Hartlep |
| 6,701,179 | B1 | 3/2004 | Martinelli et al. |
| 2001/0007918 | A1 | 7/2001 | Vilsmeier et al. |
| 2002/0095081 | A1 | 7/2002 | Vilsmeier |
| 2004/0024309 | A1 | 2/2004 | Ferre et al. |

FOREIGN PATENT DOCUMENTS

| | | | |
|---|---|---|---|
| CA | 1336451 | | 1/1988 |
| DE | 3042343 | A1 | 6/1982 |
| DE | 35 08730 | | 3/1985 |
| DE | 37 17 871 | | 5/1987 |
| DE | 38 38011 | | 11/1988 |
| DE | 3831278 | A1 | 3/1989 |
| DE | 42 13 426 | | 4/1992 |
| DE | 42 25 112 | | 7/1992 |
| DE | 4233978 | C1 | 4/1994 |
| DE | 197 15 202 | | 4/1997 |
| DE | 197 47 427 | | 10/1997 |
| DE | 197 51 761 | | 11/1997 |
| DE | 198 32 296 | | 7/1998 |
| DE | 10085137 | | 11/2002 |
| EP | 0 062 941 | | 3/1982 |
| EP | 0 119 660 | | 9/1984 |
| EP | 0 155 857 | | 1/1985 |
| EP | 0 319 844 | A1 | 1/1988 |
| EP | 0 326 768 | | 12/1988 |
| EP | 0419729 | A1 | 9/1989 |
| EP | 0350996 | A1 | 1/1990 |
| EP | 0 651 968 | A1 | 8/1990 |
| EP | 0 427 358 | | 10/1990 |
| EP | 0 501 993 | B1 | 11/1990 |
| EP | 0501993 | B1 | 11/1990 |
| EP | 0 456 103 | | 5/1991 |
| EP | 0 469 966 | A1 | 7/1991 |
| EP | 0469966 | A1 | 7/1991 |
| EP | 0 581 704 | B1 | 7/1993 |
| EP | 0655138 | B1 | 8/1993 |
| EP | 0894473 | A2 | 1/1995 |
| EP | 0 908 146 | | 10/1998 |
| EP | 0 930 046 | | 10/1998 |
| FR | 2417970 | | 2/1979 |
| FR | 2 618 211 | | 7/1987 |
| GB | 2 094 590 | | 2/1982 |
| GB | 2 164 856 | | 10/1984 |
| JP | 61-94639 | | 10/1984 |
| JP | 62-327 | | 6/1985 |
| JP | 63-240851 | | 3/1987 |
| JP | 3-267054 | | 3/1990 |
| JP | 2765738 | | 4/1991 |
| WO | WO 88/09151 | | 12/1988 |
| WO | WO 89/05123 | | 6/1989 |
| WO | WO 90/05494 | | 11/1989 |
| WO | WO/90/05494 | | 5/1990 |
| WO | WO 91/03982 | | 4/1991 |
| WO | WO 91/04711 | | 4/1991 |
| WO | WO 91/07726 | | 5/1991 |
| WO | WO 92/03090 | | 3/1992 |
| WO | WO 92/06645 | | 4/1992 |
| WO | WO 94/04938 | | 3/1994 |
| WO | WO 95/07055 | | 9/1994 |
| WO | WO 94/23647 | | 10/1994 |
| WO | WO 94/24933 | | 11/1994 |
| WO | WO 96/32059 | | 11/1995 |
| WO | WO96/11624 | | 4/1996 |
| WO | WO97/15234 | | 5/1997 |
| WO | WO 97/49453 | | 6/1997 |
| WO | WO 97/36192 | | 10/1997 |
| WO | WO 99/23956 | | 11/1997 |
| WO | WO 98/08554 | | 3/1998 |
| WO | WO 98/38908 | | 9/1998 |
| WO | WO 99/15097 | | 9/1998 |
| WO | WO 99/21498 | | 10/1998 |
| WO | WO 99/27839 | | 12/1998 |
| WO | WO 99/33406 | | 12/1998 |
| WO | WO 99/38449 | | 1/1999 |
| WO | WO 99/52094 | | 4/1999 |
| WO | WO 99/26549 | | 6/1999 |
| WO | WO 99/29253 | | 6/1999 |
| WO | WO 99/37208 | | 7/1999 |
| WO | WO 99/60939 | | 12/1999 |
| WO | WO 01/30437 | A1 | 5/2001 |

OTHER PUBLICATIONS

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Gildenberg et al., "Calculation of Stereotactic Coordinates from the Computed Tomographic Scan," Neurosurgery, vol. 10, No. 5, May 1982, pp. 580-586.
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Gueziec et al., "Registration of Computed Tomography Data to a Surgical Robot Using Fluoroscopy: A Feasibility Study," Computer Science/Mathematics, Sep. 27, 1996, 6 pages.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hatch, "Reference-Display System for the Integration of CT Scanning and the Operating Microscope," Thesis, Thayer School of Engineering, Oct. 1984, pp. 1-189.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique For Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE International Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "VI Adaption de la Methodologie a Quelques Applications Cliniques," Chapitre VI, pp. 133-148.
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Phillips et al., "Image Guided Orthopaedic Surgery Design and Analysis," Trans Inst. MC, vol. 17, No. 5, 1995, pp. 251-264.
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.
The Laitinen Stereotactic System, E2-E6.
Viant et al., "A Computer Assisted Orthopaedic System for Distal Locking of Intramedullary Nails," Proc. of MediMEC '95, Bristol, 1995, pp. 86-91.
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Weese et al., "An Approach to 2D/3D Registration of a Vertebra in 2D X-ray Fluoroscopies with 3D CT Images," pp. 119-128.
Germano, "Instrumentation, Technique and Technology", Neurosurgery, vol. 37, No. 2, Aug. 1995, pp. 348-350.
Merloz, et al., "Computer Assisted Spine Surgery", Clinical Assisted Spine Surgery, No. 337, pp. 86-96.
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
"Prestige Cervical Disc System Surgical Technique", 12 pgs.
Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 6, No. 2, pp. 144-150 (1990).
3-D Digitizing Accessories, Pixsys, Jul. 2, 1992, 6 pages.
Adams et al., Computer-Assisted Surgery, IEEE Computer Graphics & Applications, pp. 43-51, (May 1990).
Adams, L., et al., "Aide Au Reperage Tridimensionnel Pour La Chirurgie de la Base du Crane," Innov. Tech. Biol. Med., vol. 13, No. 4, pp. 409-424, 1992.
Alignment Procedure for the PixSys Two-Emitter Offset Probe for the SAC GP83d Sonic Digitizer, Pixsys, Jul. 2, 1992, 4 pages.
Bergstrom et al. Stereotaxic Computed Tomography, Am. J. Roentgenol, vol. 127 pp. 167-170 (1976).
Brown, R., M.D., A Stereotactic Head Frame for Use with CT Body Scanners, Investigative Radiology © J.B. Lippincott Company, pp. 300-304 (Jul.-Aug. 1979).
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Bucholz, Richard D., "Halo vest versus spinal fusion for cervical injury: evidence from an outcome study," J. Neurosurg 70:884-892, Jun. 1989.
Bucholz, Richard, D., M.D., "A Comparison of Sonic Digitizers Versus Light Emitting Diode-Based Localization," Interactive Image-Guided Neurosurgey, pp. 179-200, 1993.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (undated.
Germano, Isabelle M., "The NeuroStation System fir Unage-Guided, Frameless Stereotaxy," Neurosurgery, vol. 37, No. 2 Aug. 1995, pp. 348-350.
Gomez, C.R., et al., Transcranial Doppler Ultrasound Following Closed Head Injury: Vasospasm or Vasoparalysis?, Surg. Neurol., vol. 35, pp. 30-35 (1991).
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Guthrie, B.L., Graphic-Interactive Cranial Surgery: The Operating Arm System, Handbook of Stereotaxy Using the CRW Apparatus, Chapter 13, pp. 193-211 (undated.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Ng, W.S. et al., Robotic Surgery—A First-Hand Experience in Transurethral Resection of the Prostate Surgery, IEEE Eng. in Med. and Biology, pp. 120-125 (Mar. 1993).
Offset Probe for SAC GP8-3d Digitizer, 2 pages, not dated.
Penn, R.D., et al., Stereotactic Surgery with Image Processing of Computerized Tomographic Scans, Neurosurgery, vol. 3, No. 2, pp. 157-163 (Sep.-Oct. 1978).
Pixsys, 3-D Digitizing Accessories, by Pixsys (marketing brochure)(undated) (2 pages).
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).
Reinhardt, Hans. F., Neuronavigation: A Ten-Year Review, Neurosurgery, pp. 329-341 (undated).
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
Thompson, et al., A System for Anatomical and Functional Mapping of the Human Thalamus, Computers and Biomedical Research, vol. 10, pp. 9-24 (1977).
Trobraugh, J.W., et al., Frameless Stereotactic Ultrasonography: Method and Applications, Computerized Medical Imaging and Graphics, vol. 18, No. 4, pp. 235-246 (1994).
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Bucholz et al., Richard D.; "Clinical Applications of Modern Imaging Technology," SPIE vol. 1894; pp. 312-322; Jan. 19, 1993.
Bucholz et al., Richard D.; "Poster #1120, Use of An Intraoperative Optical Digitizer in A System for Free-Hand Stereotactic Surgery," Scientific Program, Am. Assoc. of Neurological Surgeons 1992 Annual Meeting, pp. 284-285; Apr. 16, 1992.
C. Hunter Shelden, M.D, et al., "Development of a computerized microstereotaxic method for localization and removal of minute CNS lesions under direct 3-D vision," J. Neurosurg 52: 21-27, 1980.
M. Peter Heilbrun, M.D., "Computer Tomography—Guided Stereotactic Systems," Computed Tomographic Stereotaxy, Ch.31 pp. 564-581, 1983.
Richard D. Bucholz, M.D. and K. Charles Cheung, M.D., "Halo vest versus spinal fusion for cervical injury: evidence from an outcome study," J. Neurosurg 70:884-892, Jun. 1989.
W. Krybus, et al., "Navigation Support for Surgery by Means of Optical Position Detection," p. 362-366, 1990.
Kurt R. Smith and Richard D. Bucholz, "Computer Methods for Improved Diagnostic Image Display Applied to Stereotactic Neurosurgery," Stereotactic Neurosurgery Display, vol. 14, pp. 371-382, 1992.
L. Adams, et al., "Aide Au Reperage Tridimensionnel Pour La Chirurgie de la Base du Crane," Innov. Tech. Biol. Med., vol. 13, No. 4, pp. 409-424, 1992.
Hans F. Reinharts, M.D., et al., "Sonic Stereometry in Microsurgical Procedures for Deep-Seated Brain Tumors and Vascular Malformations," Neurosurgery, vol. 32, No. 1, Jan. 1993 pp. 51-57.
Skip Jacques, et al., "A Computerized Microstereotactic Method to Approach, 3-Dimensionally Reconstruct, Remove and Adjuvantly Treat Small CNS Lesions," Meeting of the Amer. Soc. Stereotactic & Functional Neurosurgery, Houston 1980, Appl. Neurophysiol. 43: 176-182 (1980).
Richard D. Bucholz, M.D., and Kurt R. Smith, "A Comparison of Sonic Digitizers Versus Light Emitting Diode-Based Localization," Interactive Image-Guided Neurosurgery, pp. 179-200, 1993.
Richard D. Bucholz, et al., "Clinical Applications of Modern Imaging Technology," SPIE vol. 1894 pp. 312-322, Jan. 19, 1993.
Richard D. Bucholz, et al., "Intraoperative localization using a three dimensional optical digitizer," Proceedings of Clinical Applicatins of Modern Imaging Technology, vol. 1894, pp. 312-322, 1993.
Kevin T. Foley, et al., "Image-guided Intraoperative Spinal Localization," Intraoperative Neuroprotection: Monitoring, Ch. 19, pp. 325-340, 1996.
Kurt R. Smith, et al., "The Neurostation™—A Highly Accurate, Minimally Invasive Solution To Frameless Stereotactic Neurosurgery," Computerized Medical Imaging and Graphics, Jul.-Aug. 1994, vol. 18, No. 4, pp. 247-256.
Isabelle M. Germano, "The NeuroStation System for Image-Guided, Frameless Stereotaxy," Neurosurgery, vol. 37, No. 2, Aug. 1995, pp. 348-350.
"Alignment Procedure for the PixSys Two-Emitter Offset Probe for the SAC GP-8-3d Sonic Digitizer," PixSys, Jul. 2, 1992, 4 pages.
"3-D Digitizing Accessories," PixSys, Jul. 2, 1992, 6 pages.
Richard D. Bucholz, M.D., et al., "Poster #1120, Use of an Intraoperative Optical Digitizer in a System for Free-Hand Stereotactic Surgery," Scientific Program, Am. Assoc. of Neurological Surgeons 1992 Annual Meeting, pp. 284-285, Apr. 16, 1992.

* cited by examiner

IMAGE GUIDED AWL/TAP/SCREWDRIVER

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates generally to computer assisted image guided medical and surgical navigation systems that generate images during medical and surgical procedures indicating the relative position of various body parts, surgical implants, and instruments. In particular, the present invention relates to an instrument for use in an image guided surgery navigation system that enables the system to track both the depth and the trajectory of the instrument during surgery.

2. Background of Related Art

Computer assisted image guided medical and surgical navigation systems are known and used to generate images in order to guide a doctor during a surgical procedure. Such systems are disclosed, for example, in U.S. Pat. No. 5,383,454 to Bucholz; PCT application Ser. No. PCT/US94/04530 (Publication No. WO 94/24933) to Bucholz; and PCT application Ser. No. PCT/US95/12984 (Publication No. WO 96/11624) to Bucholz et al., incorporated herein by reference.

In general, these image guided systems use images of a body part, such as CT scans, taken before surgery to generate images on a display, such as a CRT monitor screen, during surgery for representing the position of a surgical instrument with respect to the body part. The systems typically include tracking devices such as, for example, an LED array mounted on a surgical instrument as well as a body part, a digitizer to track in real time the position of the body part and the instrument used during surgery, and a monitor screen to display images representing the body and the position of the instrument relative to the body part as the surgical procedure is performed.

There is a need in the art for a surgically navigable tool for use with these image guided systems that is simple to use and manipulate, that enables the computer tracking system to track both the trajectory of the instrument and the depth that the instrument is inserted into the body, and that is easily interchangeable with alternative drive sources such as a ratcheting handle or other instruments such as awls, taps, and screwdrivers.

SUMMARY OF THE INVENTION

It is therefore an object of the invention to provide an image guided medical instrument whose tip and trajectory can be simultaneously tracked.

It is a further object of the invention to provide an image guided medical instrument capable of generating a signal representing the trajectory and the depth of the tip of the instrument.

It is a still further object of the invention to provide an image guided medical instrument that may easily be used with any number of different tips and handles.

It is another object of the invention to provide an image guided medical instrument that is of relatively simple construction and relatively easy to use.

Additional objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a trackable medical instrument for use in a computer assisted image guided surgery system having a digitizer for tracking the position of the instrument in three dimensional space and a display providing an indication of the position of the instrument with respect to images of a body part taken preoperatively. The instrument includes a guide member having an emitter array mounted thereon for being tracked by the digitizer, and a drive shaft contained within the guide member, the drive shaft having a proximal and a distal end, the drive shaft being rotatable within the guide member while being fixable axially within the guide member, the proximal end of the drive shaft having a first connector for interchangeably receiving at least one drive source, and the distal end having a second connector for interchangeably receiving at least one instrument tip. The instrument may further include at least one instrument tip for connection to the distal end of the drive shaft and a drive handle for connection to the proximal end of the drive shaft for transmitting torque to the instrument tip to cause rotation of the instrument tip.

In another aspect of this invention, the instrument may further include a sensor which senses the removal and the connection of an instrument tip to the instrument. The sensor may be an electromechanical switch on the guide member.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
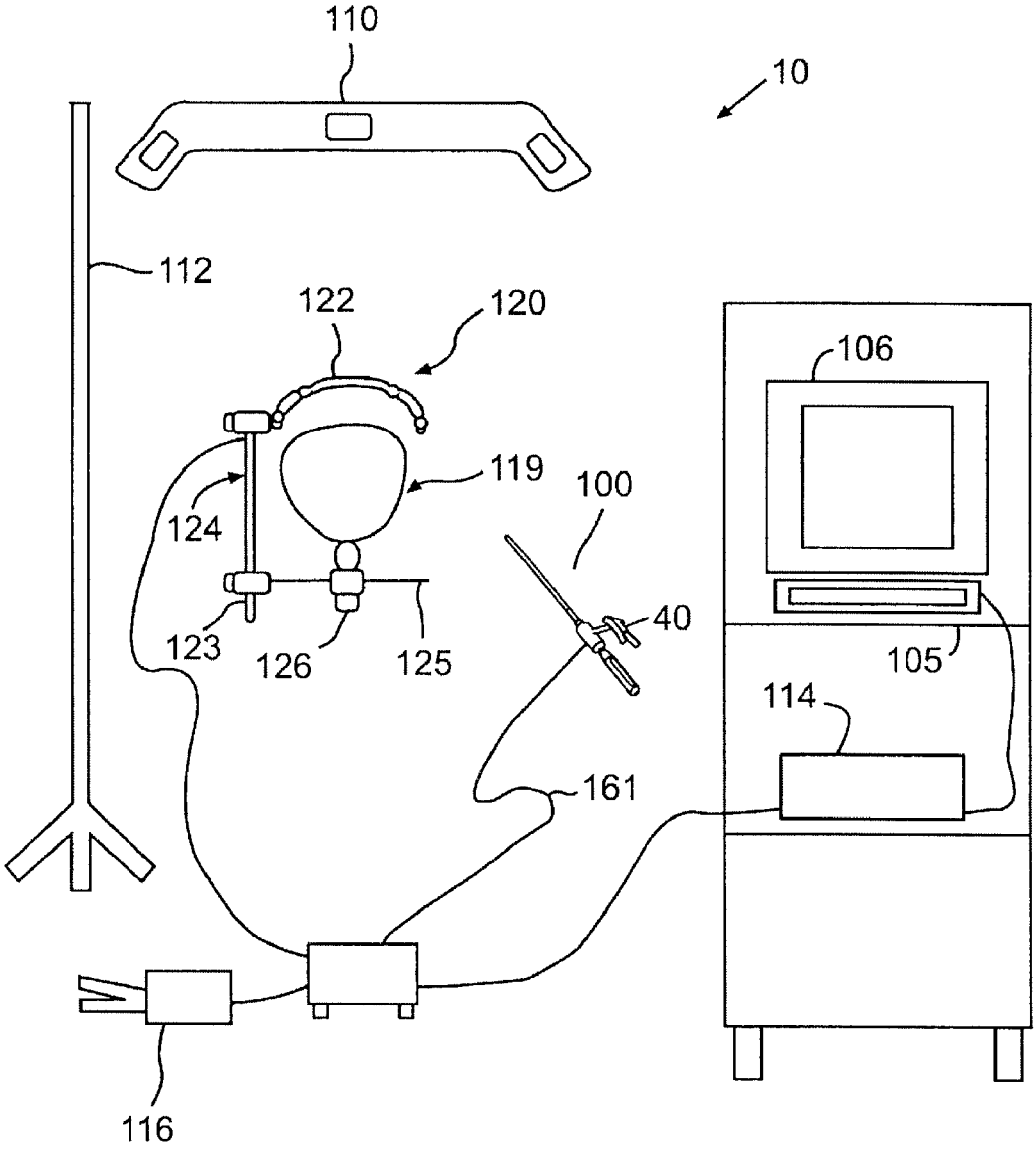
FIG. 1 is a schematic front view of a computer assisted image guided surgery system used with an instrument according to the present invention.

Reference will now be made in detail to the present preferred embodiments of the invention, examples of which are illustrated in the accompanying drawings. Wherever possible, the same reference numbers are used in the drawings and the description to refer to the same or like parts.

The medical instrument of the present invention is shown generally at 10 in FIG. 1. Instrument 100 can be used in many known computer assisted image guided surgical navigation systems such the system shown in FIG. 1 and disclosed in PCT application Ser. No. PCT/US95/12984 (Publication No. WO 96/11624) to Bucholz et al., incorporated herein by reference. A computer assisted image guided surgery system, shown at 10, generates an image for display on a monitor 106 representing the real time position of a body part and the position of instrument 100 relative to the body part.

An image may be generated on monitor 106 from an image data set stored in a controller, such as computer 108, usually generated preoperatively by some scanning technique such as by a CAT scanner or by magnetic resonance imaging. The image data set and the image generated have reference points for at least one body part. The reference points for the particularly body part have a fixed spatial relation to the particular body part.

System 10 also generally includes a processor for processing image data, shown as digitizer control unit 114. Digitizer control unit 114 is connected to monitor 106, under control of computer 108, and to instrument 100. Digitizer 114, in conjunction with a reference frame arc 120 and a sensor array 110 or other known position sensing unit, tracks the real time position of a body part, such as a cranium shown at 119 clamped in reference frame 120, and an instrument 100. Reference frame 120 has emitters 122 or other tracking means that generate signals representing the position of the various body reference points. Reference frame 120 is fixed spatially in relation to a body part by a clamp assembly indicated generally at 124,125, and 126. Instrument 100 also has a tracking device shown as an emitter array 40 which generates signals representing the position of the instrument during the procedure.

Sensor array 110, mounted on support 112, receives and triangulates the signals generated by emitters 122 and emitter array 40 in order to identify during the procedure the relative position of each of the reference points and the instrument. Digitizer 114 and computer 108 may then modify the image date set according to the identified relative position of each of the reference points during the procedure. Computer 108 may then generate an image data set representing the position of the body elements and the instrument during the procedure. System 10 may also include a foot switch 116 connected to instrument 100 and digitizer 114 for controlling operation of the system. The structure and operation of an image guided surgery system is well known in the art and need not be discussed further here.

Figure 2:
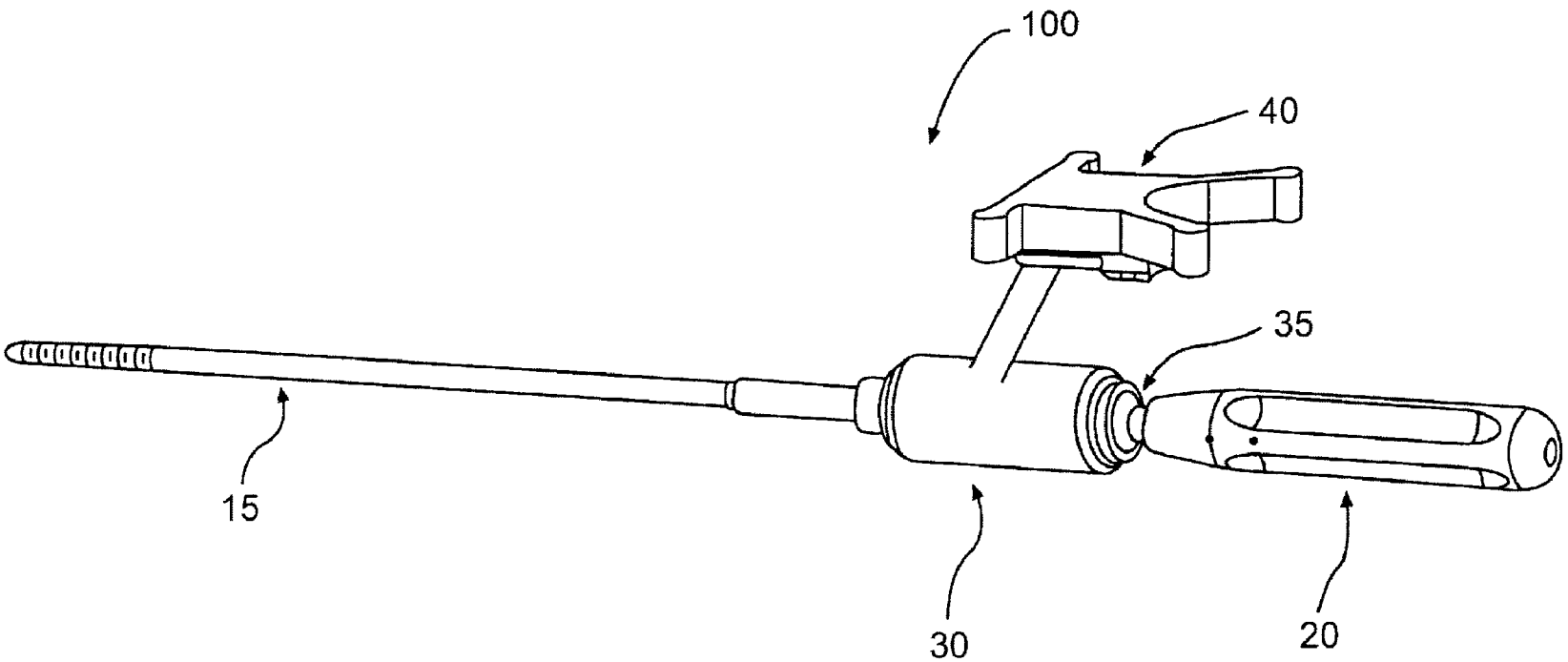
FIG. 2 is a perspective view of an instrument according to the present invention.
Figure 3:
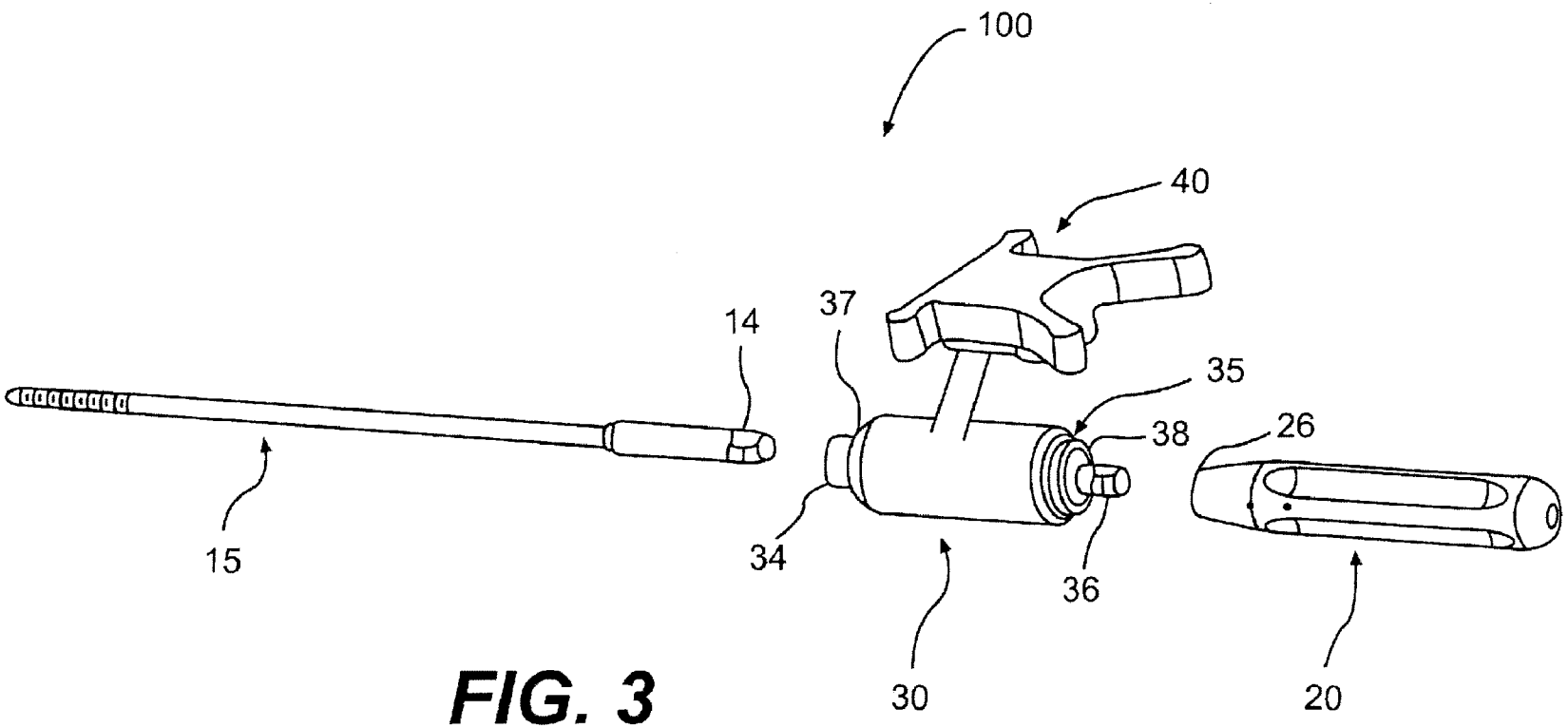
FIG. 3 is an exploded view of the instrument shown in FIG. 2.

Referring to FIGS. 2 and 3, an instrument according to the present invention is shown at 100. Instrument 100 includes a guide member 30, an interchangeable instrument tip 15, and an interchangeable driving handle 20.

Figure 5:
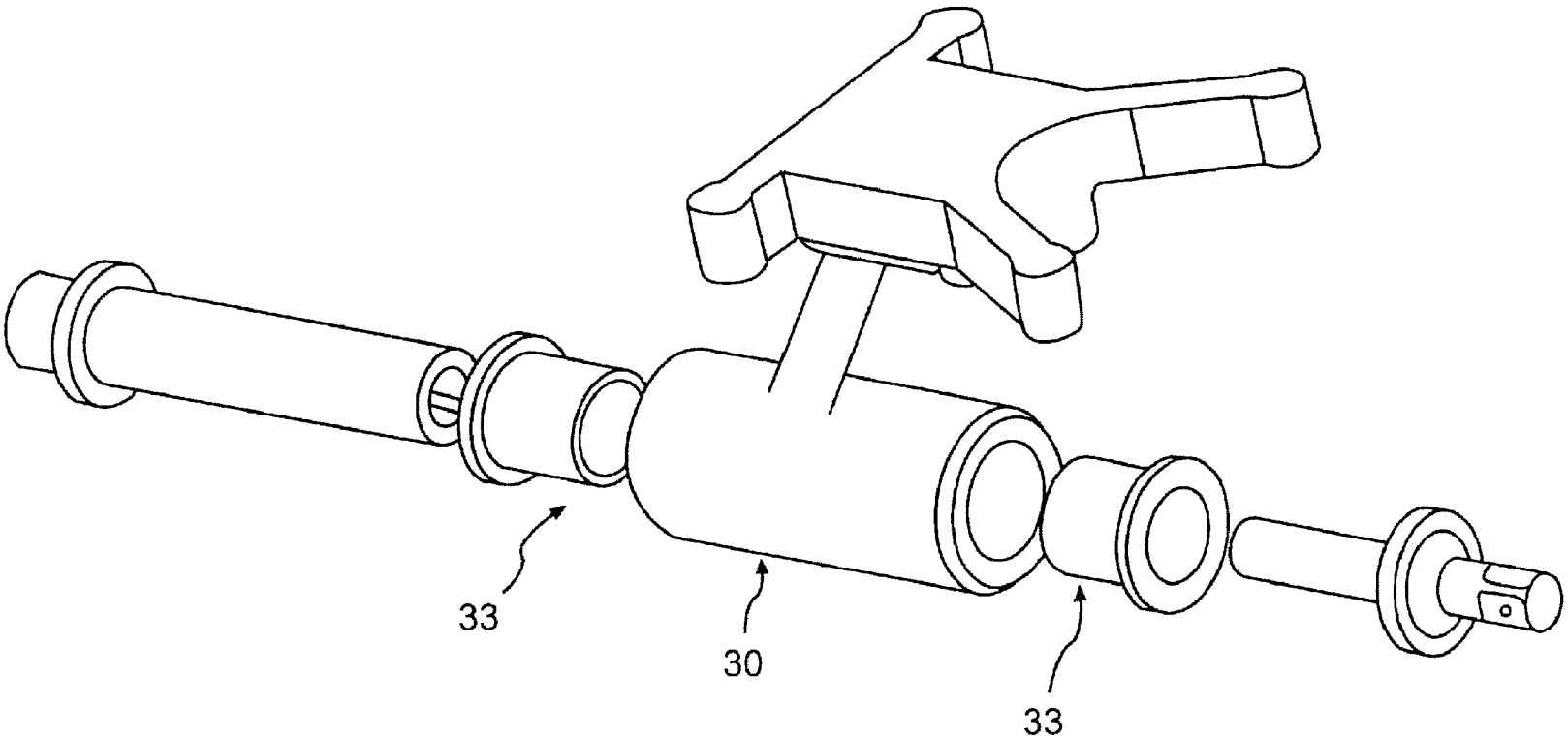
FIG. 5 is an exploded view of the portion of the instrument shown in FIG. 4.

A drive shaft 35 is housed within guide member 30 and is removably connected to an end, here the proximal end 37, to surgical instrument tip 15 and at the other end, here the distal end 38, to driving handle 20 such that torque applied manually or by motorized means to drive handle 20 is transmitted to drive shaft 35 which in turn is transmitted to tip 15. Drive shaft 35, while it could be extractable such as for service, is fixable axially in relation to guide member 30, but is rotatable within guide member 30. As shown in FIG. 5, bushings 33 may be provided at each end of guide member 30 to ensure smooth motion between drive shaft 35 and guide member 30. Guide member 30 is preferably made of stainless steel, but can also be made of titanium, aluminum or plastic. Shaft 35 is preferably made from stainless steel, titanium, or aluminum.

Figure 4:
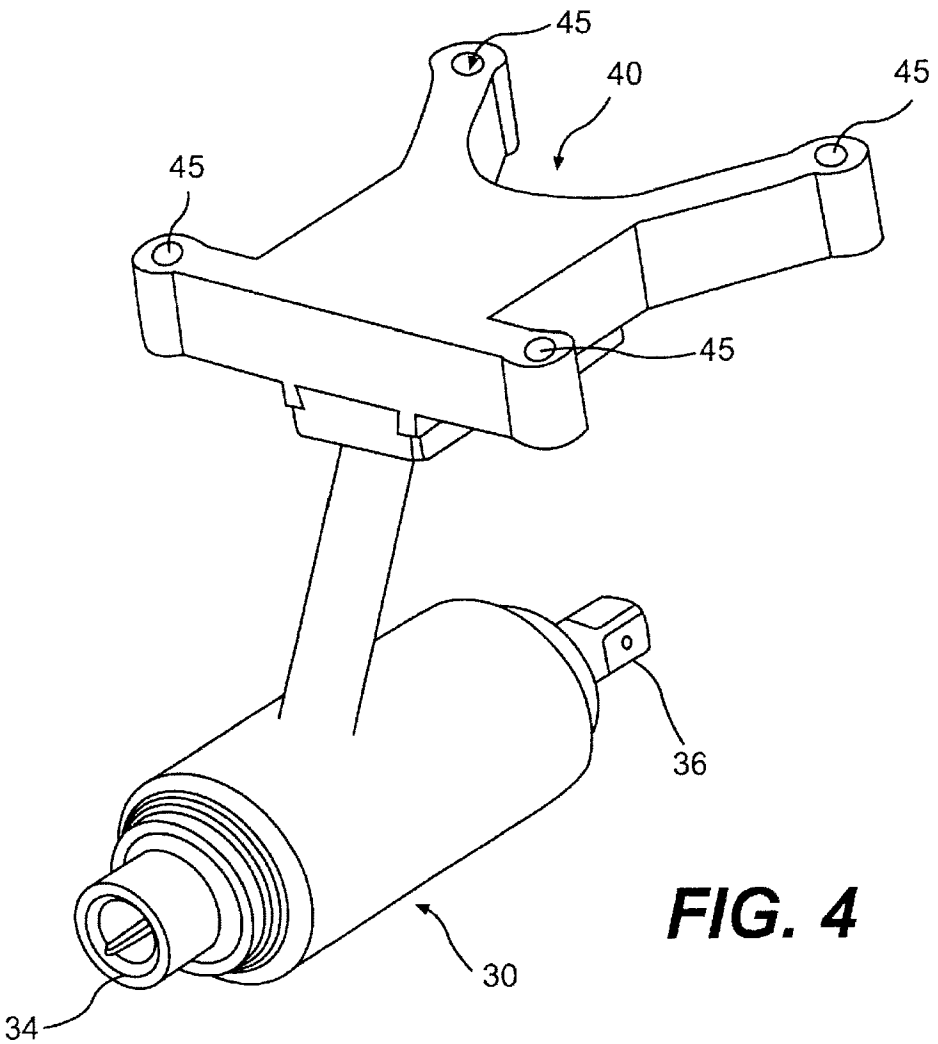
FIG. 4 is a view of a portion of the instrument shown in FIG. 2.

Instrument 100 further includes a tracking device such as emitter array 40 attached to guide member 30 for tracking the location and trajectory of instrument 100. As shown in FIG. 4, array 40 is equipped with a plurality of emitters or tracking means 45, preferably four emitters, for generating a signal representing the trajectory of instrument 100 and the depth of instrument tip 15. Preferably emitters 45 are light emitting diodes; however, other tracking devices known in the art capable of being tracked by a corresponding sensor array are within the scope of the invention. For purposes of illustration, not limitation, the tracking device may generate signals actively such as with acoustic, magnetic, electromagnetic, radiologic, and micropulsed radar systems, or passively such as with reflective surfaces.

Drive handle 20 and instrument tip 15 are shown as modular units that can be attached to drive shaft 35 with corresponding and interlocking male and female socket joints. As shown in FIGS. 3 and 4, drive shaft 35 has a female socket joint 34 for connection with a male socket 14 on tip 15, and drive shaft 35 has a male socket joint 36 for connection with a female socket joint 26 on drive handle 20. With the use of male and female socket joints, various instrument tips and various type and sized drive handles can be easily interchangeable. Instrument tip 15 could be any of a variety of instruments used in surgery such as taps, awls, and shaped tools for interacting with a work piece, such as a screwdriver for driving screws. Drive handle 20 could be any number of existing or specially designed handles and could be ratcheting, nonratcheting or motorized. Instrument tip 15 and drive handle 20 could also be permanently attached to drive shaft 35. Other suitable connection means are within the scope of the invention as well.

In operation, torque applied to drive handle 20 is transmitted through drive shaft 35 to instrument tip 15. Because drive shaft 35 is fixed axially in relation to guide member 30, guide member 30 can remain stationary while drive shaft 35 rotates without translating along the axis of drive shaft 35. The relationship between array 40 and the axis of drive shaft 35, therefore, remains constant. Instrument tip 15 is also fixed axially in relation guide member 30. As a result, the relationship between array 40 and instrument tip 15 also remains constant. Because the relationship between array 40 and tip 15 is constant, the signals emitted by emitters 45 can be used by the computer assisted image guided surgical navigation system to inform the surgeon of the position of instrument 100, indicating both the trajectory or orientation in three dimensional space of instrument 100 and the length of travel along the trajectory, i.e., the depth instrument tip 15 has been inserted into a body part.

It should be recognized that other variations or modifications may be made to provide an instrument that has an emitter array fixed axially relative to the instrument tip while allowing the instrument tip to rotate relative to the emitter array. For example, guide member 30 may also be integral with instrument tip 15 and/or drive handle 20. The array could then be fixed axially relative to the instrument and means could be provided to allow rotation of the instrument relative to the array.

As discussed above, a variety of different instrument tips may be easily interchanged on instrument 100. To use these different instrument tips, information concerning the dimensions of the different tips may be entered into computer 108. As a result, computer 108 can process the various image data for the specific instrument tip being used so that system 10 tracks the depth of the tip being used or, in the case of a screwdriver, so that system 10 tracks the depth of the screw being inserted.

System 10 may also be provided with a mechanism to prevent the system from operating after a new tip has been connected until computer 108 has been recalibrated. For example, an electromechanical switch, or other suitable sensors, could be provided on instrument 100 to provide a signal to computer 108 indicating that instrument tip 15 has been removed from instrument 100 or that a new instrument tip 15 has been coupled to instrument 100. The switch is preferably a micro switch but can be embodied by any suitable electrical or electromechanical device or sensing device capable of providing a signal in response to attachment or detachment at a particular point on guide member 30 or tip 15.

The switch may be automatically actuated when tip 15 is removed or coupled to instrument 100. Computer 108 may be operably connected to the switch, such as through cable 161, and is responsive to the operation of the switch. Alternatively, if a wireless instrument is used such as one with passive reflective surfaces in place of LED emitters, any suitable form of communication known in the art can be used. An alarm or other indication of some type, such as a message or display on monitor 106, may be generated by computer 108 indicating to the user that tip 15 has been changed. The computer 108 may further prevent the system from operating until the system has been recalibrated for the new instrument tip. Recalibration may be accomplished by touching the instrument tip to a known reference point. Recalibration of the instrument tip can be positively confirmed by means of a light emission from the emitter array 40 detected by sensor array 110 and triangulated to determine the position of the instrument tip. Alternatively, the dimensions of the instrument or tool type may be entered into computer 108 or selected from a pre-programmed list of tool dimensions or tool types. Further, recalibration could be accomplished by a fiber optic device for reading a bar code on the instrument tip, or by any other suitable recalibration technique.

It will also be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A trackable medical instrument for use in a computer assisted image guided surgery system having a digitizer for tracking the position of the instrument in three dimensional space and a display providing an indication of the position of the instrument with respect to images of a body part [take] *taken* preoperatively, the instrument comprising:

a guide member having an emitter array mounted thereon for being tracked by a digitizer; and a drive shaft contained within the guide member, the drive shaft having a longitudinal axis and a proximal and a distal end, the drive shaft being rotatable within the guide member while being fixable within the guide member in a direction of the longitudinal axis, the proximal end of the drive shaft having a first connector for interchangeably receiving at least one drive source for transmitting torque to the drive shaft causing rotation of the drive shaft relative to the guide member, and the distal end having a second connector for interchangeably receiving at least one instrument tip.

2. The instrument according to claim 1, further comprising at least one instrument tip for removable connection to the distal end of the drive shaft.

3. The instrument according to claim 2, wherein the at least [on] *one* drive source comprises a drive handle for removable connection to the proximal end of the drive shaft for transmitting torque to the drive shaft and the instrument tip to cause rotation of the instrument tip.

4. The instrument according to claim 3, wherein the drive handle and the drive shaft include a male-female socket joint to removably connect the drive shaft to the drive handle.

5. The instrument according to claim 3, wherein the drive handle includes a ratchet.

6. The instrument according to claim 3, wherein the drive handle includes a motor for imparting torque to the drive shaft.

7. The instrument according to claim 2, wherein the instrument tip and the drive shaft include a male-female socket joint to removably connect the drive shaft to the instrument tip.

8. The instrument according to claim 2, wherein the instrument tip is an awl.

9. The instrument according to claim 2, wherein the instrument tip is a tap.

10. The instrument according to claim 2, wherein the instrument tip has a shaped end for mating with a workpiece to be rotated by said drive shaft.

11. The instrument according to claim 2, wherein the instrument tip is a drill bit.

12. The instrument according to claim 1, wherein the emitter array includes at least one LED array for emitting light signals.

13. The instrument according to claim 12, wherein the LED array includes a base and a plurality of LED emitters disposed on the base.

14. The instrument according to claim 1, wherein at least one bushing is provided in the guide member to reduce friction between the guide member and drive shaft.

15. The instrument according to claim 1, wherein the instrument includes a sensor which senses the removal and connection of an instrument tip to the instrument.

16. The instrument according to 15, wherein the sensor includes an electromechanical switch on the guide member electrically connected to the system.

17. A trackable medical instrument for use in a computer assisted image guided surgery system having a digitizer for receiving signals representing a position of the instrument during surgery, a computer for processing the signals received, and a display for providing an image representing the position of the instrument in three dimensional space during surgery, the instrument comprising:

guiding means for guiding the instrument in three dimensional space, the guiding means including signaling means for providing a signal representing the trajectory of the instrument and the location of the instrument; and driving means for driving the instrument contained within the guiding means, the driving means having a longitudinal axis and being fixable in relation to the guiding means in a direction of the longitudinal axis while being rotatable in relation to the guiding means, the driving means having a first end adapted to interchangeably receive at least one medical instrument tip and an opposite end adapted to interchangeably receive at least one drive source.

18. The instrument according to claim 17, wherein the instrument includes a sensing means for sensing the removal and the connection of an instrument tip to the instrument.

19. The instrument according to 18, wherein the sensing means includes an electromechanical switch on the guiding means connected to [the] *a* means for processing.

20. The instrument according to claim 17, wherein the guiding means comprises a housing for receiving the driving means, the driving means being rotatable within the housing while being retained axially within the housing.

21. The instrument according to claim 20 wherein the signaling means comprises an LED array.

22. The instrument according to claim 21, further comprising an instrument tip for connection to the first end of the driving means.

23. The instrument according to claim 22, further comprising a drive handle for connection to the opposite end of the driving means for transmitting torque to the instrument tip to cause rotation of the instrument tip.

24. The instrument according to claim 20, wherein the driving means comprises a drive shaft having mating connectors on both ends for connection to corresponding connectors disposed on an instrument tip and a drive source.

25. The instrument according to claim 24, wherein at least one bushing is provided between the housing and the drive shaft to reduce friction between the guide handle and drive shaft.

26. The instrument according to claim 22, wherein the instrument tip is an awl.

27. The instrument according to claim 22, wherein the instrument tip is a tap.

28. The instrument according to claim 22, wherein the instrument tip has a shaped end for mating with a workpiece.

29. A trackable medical instrument for use in a computer assisted image guided surgery system having a digitizer for tracking the position of the instrument in three dimensional space and a display providing an indication of the position of the instrument with respect to images of a body part [take] *taken* preoperatively, the instrument comprising:

a guide member having an emitter array mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.

30. The instrument according to claim 29, further comprising a proximal coupler for interchangeably coupling the drive source to the drive shaft.

31. The instrument according to claim 30, wherein the proximal coupler comprises a male-female socket joint disposed on the drive shaft and the drive source to removably connect the drive source to the drive shaft.

32. The instrument according to claim 29, wherein the drive handle includes a ratchet.

33. The instrument according to claim 29, wherein the drive handle includes a motor for imparting rotary motion to the drive shaft.

34. The instrument according to claim 29, further comprising a distal coupler for interchangeably coupling the instrument tip to the drive shaft.

35. The instrument according to claim 34, wherein the distal coupler includes a male-female socket joint disposed on the drive shaft and the instrument tip to removably connect the instrument tip to the drive shaft.

36. The instrument according to claim 29, wherein the instrument tip is an awl.

37. The instrument according to claim 29, wherein the instrument tip is a tap.

38. The instrument according to claim 29, wherein the instrument tip has a shaped end for mating with a workpiece to be rotated by said drive shaft.

39. The instrument according to claim 29, wherein the instrument tip is a drill bit.

40. The instrument according to claim 29, wherein the emitter array includes at least one LED array for emitting light signals.

41. The instrument according to claim 29, wherein the at least one LED array includes a base and a plurality of LED emitters disposed on the base.

42. The instrument according to claim 29, wherein at least one bushing is provided in the guide member to reduce friction between the guide member and drive shaft.

43. A trackable medical instrument for use in a computer assisted image guided surgery system having a digitizer for tracking the position of the instrument in three dimensional space and a display providing an indication of the position of the instrument with respect to images of a body part taken preoperatively, the instrument comprising:

a guide member having a tracking device mounted thereon for being tracked by a digitizer;

a drive shaft contained within the guide member, the drive shaft having a longitudinal axis and a proximal and a distal end, the drive shaft being rotatable within the guide member while being fixable within the guide member in a direction of the longitudinal axis;

an instrument tip extending from the proximal end of the drive shaft; wherein the instrument tip rotates freely relative to the guide member while being fixable axially relative to the guide member; and a drive handle extending from the distal end of the drive shaft for guiding the instrument, including the guide member, and for imparting rotary motion to the drive shaft and the instrument tip independent of the guide member.

44. The instrument according to claim 43, wherein the tracking device includes a passive signal generator.

45. The instrument according to claim 44, wherein the instrument comprises at least one reflective surface for reflecting signals to be tracked by the digitizer.

46. The instrument according to claim 44, wherein the instrument comprises at least three reflective surfaces for reflecting signals to be tracked by the digitizer.

47. The instrument according to claim 43, further comprising a proximal coupler for interchangeably coupling the drive source to the drive shaft.

48. The instrument according to claim 47, wherein the proximal coupler comprises a male-female socket joint disposed on the drive shaft and the drive source to removably connect the drive source to the drive shaft.

49. The instrument according to claim 43, further comprising a distal coupler for interchangeably coupling the instrument tip to the drive shaft.

50. The instrument according to claim 49, wherein the distal coupler includes a male-female socket joint disposed on the drive shaft and the instrument tip to removably connect the instrument tip to the drive shaft.

*51. A trackable medical instrument for use in a computer assisted image guided surgery system having a digitizer for tracking the position of the instrument in three dimensional space and a display providing an indication of the position of the instrument with respect to images of a body part taken preoperatively, the instrument comprising:*

*a guide member having an emitter array mounted thereon for being tracked by a digitizer; and*

*a drive shaft contained within the guide member, the drive shaft having a longitudinal axis and a proximal and a distal end, the drive shaft being rotatable within the guide member while being fixable within the guide member in a direction of the longitudinal axis, the proximal end of the drive shaft having a first connector for receiving at least one drive source for transmitting torque to the drive shaft causing rotation of the drive shaft relative to the guide member, and the distal end having a second connector for receiving at least one instrument tip.*

*52. A trackable medical instrument for use with a surgical navigation system, the trackable medical instrument comprising:*

*a surgical implement having a distal end;*

*a guide member coupled to the surgical implement; and*

*a tracking device mounted to the guide member, wherein the tracking device is rotatable relative to the surgical implement wherein the relationship between the tracking device and the distal end of the surgical implement remains substantially constant upon rotating the tracking device relative to the surgical implement and the substantially constant relationship enables the distal end of the surgical implement to be tracked by the surgical navigation system.*

*53. The trackable medical instrument as defined in claim 52, wherein the substantially constant relationship between the tracking device and the distal end of the surgical implement is a distance between the tracking device and the distal end of the surgical implement.*

*54. The trackable medical instrument as defined in claim 52, wherein the surgical implement comprises a proximal end comprising a coupling member.*

*55. The trackable medical instrument as defined in claim 52, wherein the substantially constant relationship enables both orientation in three-dimensional space of the surgical implement and a depth the distal end of the surgical implement has been inserted into a body part to be tracked by the surgical navigation system.*

*56. The trackable medical instrument as defined in claim 52, wherein the tracking device is fixed axially with respect to the distal end of the surgical implement.*

*57. The trackable medical instrument as defined in claim 52, wherein the surgical implement is rotatably coupled to the guide member.*

*58. The trackable medical instrument as defined in claim 57, wherein the tracking device is fixedly secured to the guide member.*

*59. The trackable medical instrument as defined in claim 52, wherein the surgical implement and the guide member are integral.*

*60. The trackable medical instrument as defined in claim 52, wherein the tracking device is selected from at least one of a LED, a reflector, an acoustic device, a magnetic device, an electromagnetic device, a radiologic device, a micropulsed radar device or combinations thereof.*

*61. The trackable medical instrument as defined in claim 52, wherein the tracking device is one of either an active tracking device or a passive tracking device.*

*62. The trackable medical instrument as defined in claim 52, wherein the surgical implement is selected from at least one of a tap, an awl, a driving instrument, a drill, or combinations thereof.*

*63. The trackable medical instrument as defined in claim 52, further comprising a drive source coupled to the guide member to drive the surgical implement.*

*64. The trackable medical instrument as defined in claim 63, wherein the drive source, the surgical implement and the guide member are integral.*

*65. The trackable medical instrument as defined in claim 63, wherein the drive source is a drive handle.*

*66. The trackable medical instrument as defined in claim 65, wherein the drive handle includes a ratchet.*

*67. The trackable medical instrument as defined in claim 63, wherein the drive source is a motor.*

*68. The trackable medical instrument as defined in claim 63, further comprising a drive shaft housed within the guide member, wherein the drive source is operable to rotate the drive shaft to rotate the surgical implement.*

*69. The trackable medical instrument as defined in claim 68, wherein the surgical implement and the drive source are removable from the drive shaft.*

*70. The trackable medical instrument as defined in claim 52, wherein the tracking device includes a plurality of tracking devices.*

*71. The trackable medical instrument as defined in claim 52, further comprising a sensor operable to sense a removal and connection of the surgical implement to the medical instrument.*

*72. The trackable medical instrument as defined in claim 52, further comprising a bushing operable to allow the tracking device to be rotated relative to the surgical implement.*

*73. The trackable medical instrument as defined in claim 72, wherein the bushing is positioned within the guide member.*

*74. The trackable medical instrument as defined in claim 52, further comprising a plurality of surgical implements each operable to be interchangeably coupled to the guide member.*

*75. The trackable medical instrument as defined in claim 52, wherein the tracking device includes a tracking array mounted to the guide member.*

*76. The trackable medical instrument as defined in claim 52, wherein the guide member includes a mount for mounting the tracking device.*

*77. The trackable medical instrument as defined in claim 76, wherein the guide member further includes an elongated tubular body with the guide member mount extending from the elongated tubular body.*

*78. A trackable medical instrument for use with a surgical navigation system, the trackable medical instrument comprising:*

*a surgical implement having a distal end;*

*a guide member coupled to the surgical implement;*

*a tracking device mounted to the guide member; and*

*a means for rotating the tracking device relative to the surgical implement; wherein the relationship between the tracking device and the distal end of the surgical implement remains substantially constant upon rotating the tracking device relative to the surgical implement and the substantially constant relationship enables the distal end of the surgical implement to be tracked.*

*79. The trackable medical instrument as defined in claim 78, wherein the surgical implement is rotatably coupled to the guide member.*

*80. The trackable medical instrument as defined in claim 78, wherein the surgical implement is integral with the guide member.*

*81. The trackable medical instrument as defined in claim 78, wherein the tracking device is fixed axially with respect to the distal end of the surgical implement.*

*82. The trackable medical instrument as defined in claim 78, further comprising a drive source coupled to the guide member to drive the surgical implement.*

*83. The trackable medical instrument as defined in claim 78, wherein the tracking device is a passive reflective tracking device and the medical instrument is a wireless instrument.*

*84. The trackable medical device as defined in claim 78, wherein the surgical implement and the guide member extend along a longitudinal axis.*

*85. The trackable medical instrument as defined in claim 78, further comprising a sensor operable to sense a removal and connection of the surgical implement to the medical instrument.*

*86. A trackable medical instrument for use with a surgical navigation system, the trackable medical instrument comprising:*

*a surgical implement having a distal end;*

*a handle positioned near a proximal end of the medical instrument;*

*a guide member coupled to the surgical implement and handle; and*

*a tracking device mounted to the guide member, wherein the tracking device is rotatable relative to the surgical implement; and the relationship between the tracking device and the distal end of the surgical implement remains substantially constant upon rotating the tracking device relative to the surgical implement.*

*87. The trackable medical instrument as defined in claim 86, wherein the handle is a drive handle.*

*88. The trackable medical instrument as defined in claim 86, wherein the surgical implement is selected from at least one of a tap, an awl, a driving instrument, a drill, or combinations thereof.*

* * * * *

UNITED STATES PATENT AND TRADEMARK OFFICE

CERTIFICATE OF CORRECTION

PATENT NO. : RE43,328 E
APPLICATION NO. : 10/062265
DATED : April 24, 2012
INVENTOR(S) : Kevin T. Foley et al.

It is certified that error appears in the above-identified patent and that said Letters Patent is hereby corrected as shown below:

In the Specification

Column 1, line 8, above the heading, "BACKGROUND OF THE INVENTION" insert:

-- Notice: More than one reissue application has been filed for the reissue of patent 6,021,343. The reissue applications are application number 10/062,265, filed January 31, 2002, now U.S. Reissued Patent No. 43,328, and application number 13/453,709, filed April 23, 2012, which is a continuation reissue application of the 10/062,265 application and claims the benefit of the prior reissue application. --

Signed and Sealed this
Twelfth Day of November, 2013

Teresa Stanek Rea

Teresa Stanek Rea
*Deputy Director of the United States Patent and Trademark Office*